US00PP13180P2

(12) United States Plant Patent
Strope

(10) Patent No.: US PP13,180 P2
(45) Date of Patent: Nov. 5, 2002

(54) NEW GUINEA IMPATIENS PLANT NAMED 'BALCEBSAFO'

(75) Inventor: Kerry M. Strope, Pismo Beach, CA (US)

(73) Assignee: Ball FloraPlant, a division of Ball Horticultural corporation, West Chicago, IL (US)

( * ) Notice: Subject to any disclaimer, the term of this patent is extended or adjusted under 35 U.S.C. 154(b) by 0 days.

(21) Appl. No.: 09/772,824

(22) Filed: Jan. 30, 2001

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct cultivar of New Guinea impatiens plant named Balcebsafo, characterized by its large light salmon flowers, dark green foliage, compact upright and mounded habit and excellent basal branching.

1 Drawing Sheet

BOTANICAL CLASSIFICATION

*Impatiens hawkeri* cultivar 'Balscebsafo'.

BACKGROUND OF INVENTION

The present invention comprises a new and distinct New Guinea impatiens plant, botanically known as *Impatiens hawkeri*, and hereinafter referred to by the cultivar name 'Balcebsafo'.

The new cultivar was developed by the inventor through a controlled breeding program during 1997 at Arroyo Grande, Calif. The objective of the breeding program was to develop cultivars with numerous large flowers, compact to moderate growth habit and excellent basal branching.

The female (seed) parent of 'Balcebsafo' was the proprietary *Impatiens hawkeri* cultivar designated '1199' (non-patented), characterized by its compact habit, lavender flowers and dark green foliage. The male (pollen) parent of 'Balcebsafo' was the *Impatiens hawkeri* cultivar 'Toga' (U.S. Plant Pat. No. 10,304) characterized by its compact habit, lavender flowers and dark green foliage. 'Balcebsafo' was discovered and selected in December 1997 by the inventor as a flowering plant within the progeny of the stated cross.

Asexual reproduction of the new cultivar by terminal cuttings has demonstrated that the characteristics of the new cultivar as herein described are firmly fixed and are retained through successive generations of such asexual propagation. The new cultivar was asexually reproduced in Arroyo Grande, Calif. and West Chicago, Ill.

SUMMARY OF INVENTION

It was found that the cultivar of the present invention:

(a) exhibits large round light salmon flowers, (b) forms dark green foliage, (c) exhibits a good basal branching character, and (d) exhibits a medium upright mounded growth habit.

The new cultivar of the present invention can be compared to 'Celebration Deep Coral' (U.S. Plant Pat. No. 9,214). In side by side comparisons, plants of the new cultivar differ from 'Celebration Deep Coral' by the following characteristics: it is found that the new cultivar is more compact, has longer internodes, longer petioles and lighter flower color. The new cultivar can also be compared to 'Celebrette Peach' (U.S. Plant Pat. No. 10,108). In side by side comparisons it is found that the new cultivar is more compact, has shorter peduncles, larger, pinker flowers, longer internodes and different foliage coloration. A detailed comparison can be found below in Table A.

TABLE A

| CHARACTERISITIC | 'BALCEBSAFO' | CELEBRETTE PEACH |
|---|---|---|
| PLANT HEIGHT | 18.4 cm | 21 cm |
| STEM COLOR | 185A | 53B |
| BRANCH LENGTH | 16.2 cm | 18.3 cm |
| INTERNODE LENGTH | 6.9 cm | 2.6 cm |
| MATURE LEAF LENGTH × WIDTH | 8.2 cm × 3.1 cm | 9 cm × 3.4 cm |
| MATURE LEAF COLOR-UPPER SURFACE | 139A WITH VENATION OF LIGHT GREEN | 136A WITH VENATION OF 63A |
| MATURE LEAF COLOR-LOWER SURFACES | 191 A WITH VENATION OF 184B | 183C WITH VENATION OF 185B |
| PETIOLE LENGTH | 1.2 cm | 1.5 cm |
| FULLY OPENED PETAL COLOR-UPPER SURFACE | 48B GRADUALLY FADING THROUGH 48C, 48D AND 39D TO BASE OF 51B | SUPERIOR PETAL: 41A AT EDGE; 63B AT BASE. OTHER PETALS: 41A AT EDGE, FADING THROUGH 63D TO 63A AT BASE |
| PEDUNCLE LENGTH | 4.2 cm | 5.4 cm |
| PEDUNCLE COLOR | 53A | 144D |
| FLOWER DIAMETER | 6.4 cm | 5.5 cm |
| SPUR COLOR | 53A | 53C |
| SPUR LENGTH | 5.6 cm | 4.3 cm |
| POLLEN COLOR | 19B | 11C |

| CHARACTERISITIC | CELEBRATION DEEP CORAL |
|---|---|
| PLANT HEIGHT | 27.1 cm |
| STEM COLOR | 187D |
| BRANCH LENGTH | 23.3 cm |
| INTERNODE LENGTH | 5.8 cm |
| MATURE LEAF LENGTH × WIDTH | 8.4 cm × 3.5 cm |

TABLE A-continued

| | |
|---|---|
| MATURE LEAF COLOR-UPPER SURFACE | 187 A WITH MIDVEIN OF 45B |
| MATURE LEAF COLOR-LOWER SURFACES | 187C |
| PETIOLE LENGTH | .9 cm |
| FULLY OPENED PETAL COLOR-UPPER SURFACE | 50A |
| PEDUNCLE LENGTH | 4.9 cm |
| PEDUNCLE COLOR | 53D |
| FLOWER DIAMETER | 6.8 cm |
| SPUR COLOR | 53C |
| SPUR LENGTH | 5.2 cm |
| POLLEN COLOR | 19B |

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown in a greenhouse at West Chicago, Ill., U.S.A.

DETAILED DESCRIPTION

The 'Balcebsafo' cultivar has not been observed under all possible environmental conditions to date. Accordingly, it is possible that the phenotype may vary somewhat with variations in the environment, such as temperature, light intensity, and day length.

The chart used in the identification of colors described herein is the R.H.S. Colour Chart of The Royal Horticultural Society, London, England. The color values were determined on Aug. 30, 2000 between 1:00 and 3:00 p.m. under natural daylight conditions. The plants were ten (10) weeks old and were produced from cuttings taken from stock plants and were grown in 10 cm pots under greenhouse conditions comparable to those used in commercial practice while utilizing a soilless growth medium and maintaining temperatures of approximately 72° F. during the day and approximately 65° F. during the night.

Parentage: Proprietary seedling '1199'×'Toga'.

Propagation:

*Type cutting.*—Terminal tip.

*Time to initiate roots.*—Approximately 7–14 days with the shorter times generally being experienced in the summer and the longer times in the winter.

*Time to develop roots.*—Approximately 21 days.

*Rooting habit.*—Fibrous, branching.

Plant description:

*Habit of growth.*—Moderately vigorous. A mature plant, 8 to 10 weeks after planting of a rooted cutting, measures approximately 18.4 cm in height and approximately 33.4 cm in width.

*Form.*—Upright and mounded.

*Foliage.*—Leaves are simple, lanceolate, acuminate apex, attenuate base, serrate and ciliate margin. Texture: smooth. Size of mature foliage: approximately 8.2 cm in length, approximately 3.1 cm in width. Color of mature foliage: upper surface is 139A with venation of 144D; lower surface is 191A with venation of 184B. Petiole: Length: approximately 1.2 cm. Color: 184C.

*Stem.*—Color: 185A. Internode length: approximately 6.9 cm.

Flower description:

*Flowering habit.*—Freely flowering.

*Natural flowering season.*—Year round in greenhouse environment. Flowering is continuous from spring until fall in the garden.

*Bud shape, size, color.*—Shape: Ovate. Length: 1 cm. Color: 60B.

*Flower longevity.*—Approximately seven days.

*Flowers borne.*—Above foliage arising from leaf axils.

*Flower color.*—Upper surface of petals is 48B at edges gradually fading through 48C, 48D and 39D to bases of 51B; lower surface is between 40A and 50C with midvein of 51B.

*Quantity of flowers.*—Approximately 2 flowers and 5 buds per stem.

*Petals.*—Number: Five. Shape: Obovate, superior petal has broad base, other four petals have narrow base. Approximate size: Superior petal width, 4.1 cm; superior petal length, 2.8 cm. Lateral petal width, 2.7 cm; lateral petal length, 2.8 cm; lower petals width, 3.1 cm, lower petal length, 3.4 cm.

*Flower diameter.*—Approximately 6.4 cm.

*Spur.*—Origin: from inferior sepal; Length: Approximately 5.6 cm. Color: 53A. Shape: Very Slightly Curved.

*Peduncle.*—Length: Approximately 4.2 cm. Color: 53A.

*Flower buds.*—Length: approximately 2 cm, width: approximately 1.2 cm when first showing color.

*Reproductive organs.*—Androecium: five stamens, anthers are fused together forming one organ that surrounds the pistil. Generally, the anthers shed pollen prior to the stigma becoming receptive, pollen color is 19B. Gynoecium: the stigma color is 154D the style color is 144A and the ovary color is 144A.

*Anther shape, size, color.*—Anther Shape: Hooded, Anther size: 2.2 mm. Anther color: 20B.

*Pistil length, stigma color.*—Pistil Length: 3 mm. Stigma color: 70B.

*Seed production.*—Seed production has not been observed.

Disease resistance: Resistance to pathogens has not been observed.

I claim:

1. A new and distinct cultivar of New Guinea Impatiens plant named 'Balcebsafo' substantially as herein shown and described, which:

(a) exhibits attractive, large round light salmon flowers, (b) forms dark green foliage, (c) exhibits a good basal branching character, and exhibits a medium upright mounded growth habit.

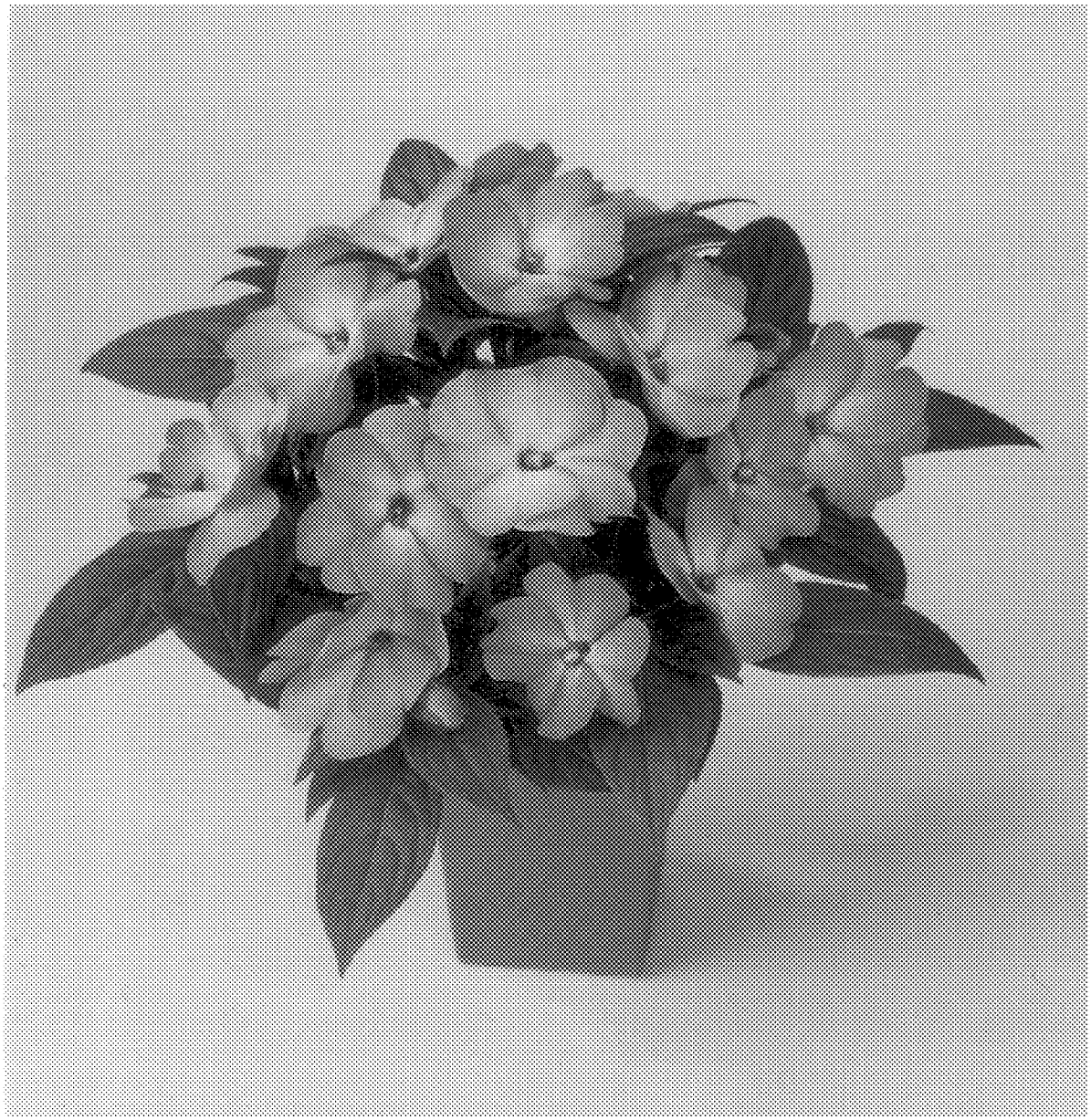

* * * * *